United States Patent
Kikuchi (10) Patent No.: US 11,657,099 B2
(45) Date of Patent: May 23, 2023

(54) INFORMATION PROCESSING APPARATUS EVALUATING SIMILARITY BETWEEN MEDICAL DATA, INFORMATION PROCESSING METHOD, AND STORAGE MEDIUM

(71) Applicant: CANON KABUSHIKI KAISHA, Tokyo (JP)

(72) Inventor: Toru Kikuchi, Hino (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 0 days.

(21) Appl. No.: 16/928,891

(22) Filed: Jul. 14, 2020

(65) Prior Publication Data
US 2021/0020310 A1    Jan. 21, 2021

(30) Foreign Application Priority Data
Jul. 17, 2019    (JP) .............................. JP2019-132264

(51) Int. Cl.
*G16H 50/20*    (2018.01)
*G16H 50/70*    (2018.01)
(Continued)

(52) U.S. Cl.
CPC ............ *G06F 16/906* (2019.01); *A61B 6/032* (2013.01); *A61B 6/5217* (2013.01);
(Continued)

(58) Field of Classification Search
CPC ........ G16H 50/70; G16H 50/30; G16H 50/50; G06N 3/0454
See application file for complete search history.

(56) References Cited

U.S. PATENT DOCUMENTS

2020/0111570 A1*    4/2020    Tran ....................... G06N 20/20

FOREIGN PATENT DOCUMENTS

| JP | 3085724 B2 | 9/2000 | |
| JP | 4104036 B2 | 6/2008 | |
| WO | WO-2015039021 A2 * | 3/2015 | ........... A61B 5/7264 |

OTHER PUBLICATIONS

Kumar, Ashnil, et al. "An ensemble of fine-tuned convolutional neural networks for medical image classification." IEEE journal of biomedical and health informatics 21.1 (2016): 31-40. (Year: 2016).*

* cited by examiner

*Primary Examiner* — Linh Giang Le
*Assistant Examiner* — Constantine Siozopoulos
(74) *Attorney, Agent, or Firm* — Canon U.S.A., Inc. IP Division (57) ABSTRACT

An information processing apparatus according to an exemplary embodiment includes a likelihood acquisition unit, a first evaluation unit, a determination unit, and a second evaluation unit. The likelihood acquisition unit is configured to acquire class likelihood for first medical data given a correct answer label, by using a first classifier for classifying medical data. The first evaluation unit is configured to evaluates a degree of deviance based on the class likelihood acquired by the likelihood acquisition unit and a class answer corresponding to the correct answer label. The determination unit is configured to determine whether the degree of deviance by the first evaluation unit satisfies a predetermined criterion. The second evaluation unit is configured to, based on second medical data satisfying the predetermined criterion, out of the first medical data, evaluate a similarity between the second medical data and third medical data to be subjected to classification.

16 Claims, 10 Drawing Sheets

(51) Int. Cl.
*G06F 16/906* (2019.01)
*G06F 16/28* (2019.01)
*G16H 70/20* (2018.01)
*G16H 30/40* (2018.01)
*A61B 6/03* (2006.01)
*G06N 5/048* (2023.01)
*A61B 6/00* (2006.01)
*G16H 30/20* (2018.01)
*G06F 18/214* (2023.01)
*G06F 18/21* (2023.01)
*G06V 10/25* (2022.01)
*G06V 10/764* (2022.01)
*G06V 10/774* (2022.01)
*G06V 10/82* (2022.01)

(52) U.S. Cl.
CPC .......... *G06F 16/285* (2019.01); *G06F 18/214* (2023.01); *G06F 18/2193* (2023.01); *G06N 5/048* (2013.01); *G06V 10/25* (2022.01); *G06V 10/764* (2022.01); *G06V 10/774* (2022.01); *G06V 10/82* (2022.01); *G16H 30/20* (2018.01); *G16H 30/40* (2018.01); *G16H 50/20* (2018.01); *G16H 50/70* (2018.01); *G16H 70/20* (2018.01)

INFORMATION PROCESSING APPARATUS EVALUATING SIMILARITY BETWEEN MEDICAL DATA, INFORMATION PROCESSING METHOD, AND STORAGE MEDIUM

BACKGROUND

Field

One disclosed aspect of the embodiments relates to an information processing apparatus for evaluating input data to a classifier, an information processing method, and a non-transitory storage medium.

Description of the Related Art

Computer Aided Diagnosis (CAD) systems are known that analyze medical images and present information for supporting radiographic interpretation to a doctor. A certain CAD system classifies the diagnostic name as a candidate for differential diagnosis based on medical images and presents resultant information. Such a CAD system is implemented by performing machine learning of a classifier by using teacher data including a pair of a medical data piece and a correct diagnostic name (correct answer label). If the number of pieces of teacher data is insufficient for a target issue, it may be impossible to perform sufficient machine learning of the classifier.

The CAD system discussed in Japanese Patent No. 3085724 selects an abnormality detection unit for detecting abnormality such as a lung nodule according to medical data attributes such as an inspection portion and modality. In this case, if a medical data type which cannot be detected as abnormality by the abnormality detection unit is specified, the CAD system outputs information indicating that abnormality detection is impossible for the medical data.

The CAD system discussed in Japanese Patent No. 4104036 stores a support result of lesion detection by an abnormality detection processing system and a correction result after the correction of the support result by a doctor in such a manner that these results are associated with each other. Then, the CAD system performs quantitative evaluation on the support processing performance of the system.

Even if the attributes of the teacher data used for the learning of the classifier are identical to the attributes of input data, it is difficult to evaluate medical data having features not sufficiently learned by the classifier.

Although the CAD system is capable of evaluating the performance of the classifier by using the correction result by a doctor, it is difficult to evaluate medical data having features not sufficiently learned by the classifier.

SUMMARY

An information processing apparatus according to an exemplary embodiment includes a likelihood acquisition unit, a first evaluation unit, a determination unit, and a second evaluation unit. The likelihood acquisition unit is configured to acquire class likelihood for first medical data given a correct answer label, by using a first classifier for classifying medical data. The first evaluation unit is configured to evaluates a degree of deviance based on the class likelihood acquired by the likelihood acquisition unit and a class answer corresponding to the correct answer label. The determination unit is configured to determine whether the degree of deviance by the first evaluation unit satisfies a predetermined criterion. The second evaluation unit is configured to, based on second medical data satisfying the predetermined criterion, out of the first medical data, evaluate a similarity between the second medical data and third medical data to be subjected to classification.

Further features of the disclosure will become apparent from the following description of exemplary embodiments with reference to the attached drawings.

DESCRIPTION OF THE EMBODIMENTS

The disclosure will be described in detail below based on exemplary embodiments of the disclosure with reference to the accompanying drawings. Unless otherwise noted, items which have been described in other exemplary embodiments are assigned the same reference numerals, and redundant descriptions thereof will be omitted. The configurations of the following exemplary embodiments are to be considered as illustrative, and the disclosure is not limited to the illustrated configurations.

A first exemplary embodiment will be described below centering on an information processing apparatus as a Computer Aided Diagnosis (CAD) system for classifying the diagnostic name for a lung nodule shadow on a chest X-ray Computed Tomography (CT) image. The information processing apparatus according to the present exemplary embodiment evaluates the deviance between the class likelihood obtained by a classifier and a correct answer or response (correct answer or response label), evaluates the similarity between data determined based on the deviance and processing target data, and notifies the user of the evaluation result. The class likelihood refers to the accuracy assigned to each class in classification by a classifier based on machine learning. A class refers to a classification target by a classifier. The diagnostic name is an example of a class. The user can select whether to continue processing based on the notification.

(System Configuration)

Figure 1:
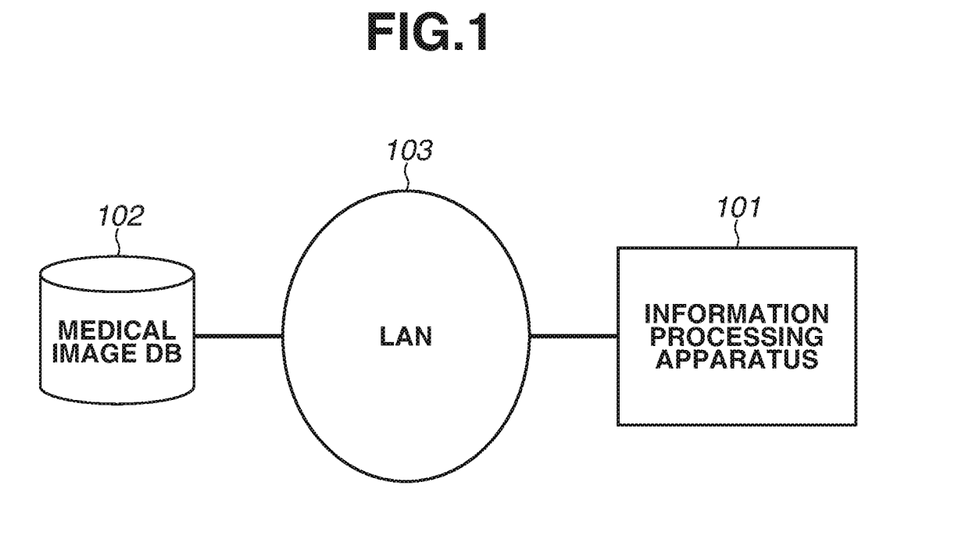
FIG. 1 illustrates a system configuration of an information processing system including an information processing apparatus according to first and second exemplary embodiments.

FIG. 1 illustrates a system configuration of an information processing system including an information processing apparatus according to the present exemplary embodiment.

Referring to FIG. 1, the information processing system includes a medical image database (hereinafter referred to as a medical image DB) 102, an information processing apparatus 101, and a Local Area Network (LAN) 103.

The medical image DB 102 stores medical images captured by a medical imaging apparatus such as a Computed Tomography (CT) apparatus, and medical data including the diagnostic name of the medical images. The medical image DB 102 provides known database functions for retrieving and acquiring medical data via the LAN 103. The configuration of the medical data stored in the medical image DB 102 will be described blow with reference to FIG. 3.

(Hardware Configuration)

Figure 2:
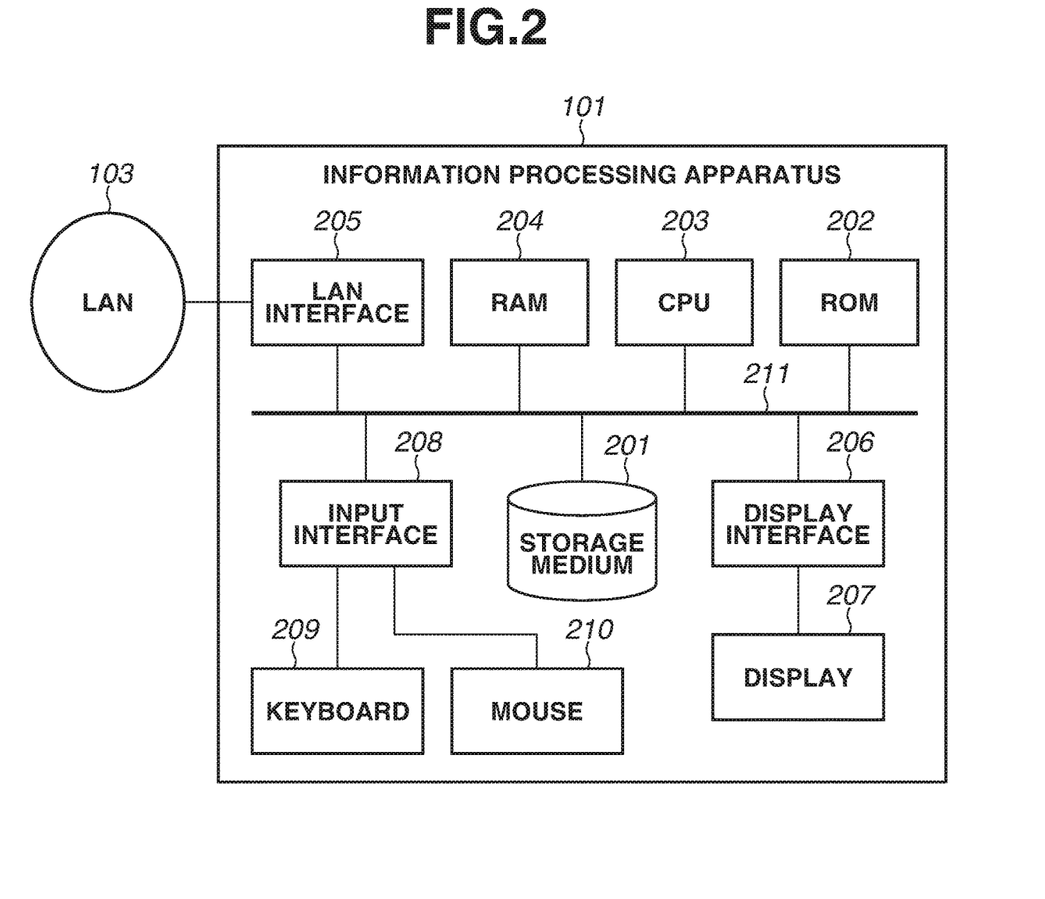
FIG. 2 illustrates a hardware configuration of the information processing apparatus according to the first and second exemplary embodiments.

FIG. 2 illustrates a hardware configuration of an information processing apparatus 101 according to the present exemplary embodiment.

Referring to FIG. 2, a storage medium 201 is a hard disk drive (HDD) for storing an Operating System (OS), processing programs for performing various kind of processing according to the present exemplary embodiment, and various kinds of information. A read only memory (ROM) 202 stores programs for initializing the hardware and activating the OS, such as the Basic Input Output System (BIOS). A Central Processing Unit (CPU) 203 performs calculation processing or operations when executing the BIOS, OS, and processing programs. A Random Access Memory (RAM) 204 temporarily stores information, which may include program/instructions and/or data, when the CPU 203 executes a program to perform calculations or operations described in the following. A LAN interface 205 conforming to the Institute of Electrical and Electronic Engineers (IEEE) 802.3ab standard performs communication via the LAN 103. A display 207 displays a display screen. A display interface 206 converts screen information to be displayed on the display 207 into signals and output the signals. A keyboard 209 is used to perform key input operations. A mouse 210 is used to specify a coordinate position on the screen and input a button operation. An input interface 208 receives signals from the keyboard 209 and the mouse 210. An internal bus 211 is used for communication among the above-described blocks.

(Medical Data Configuration)

Figure 3:
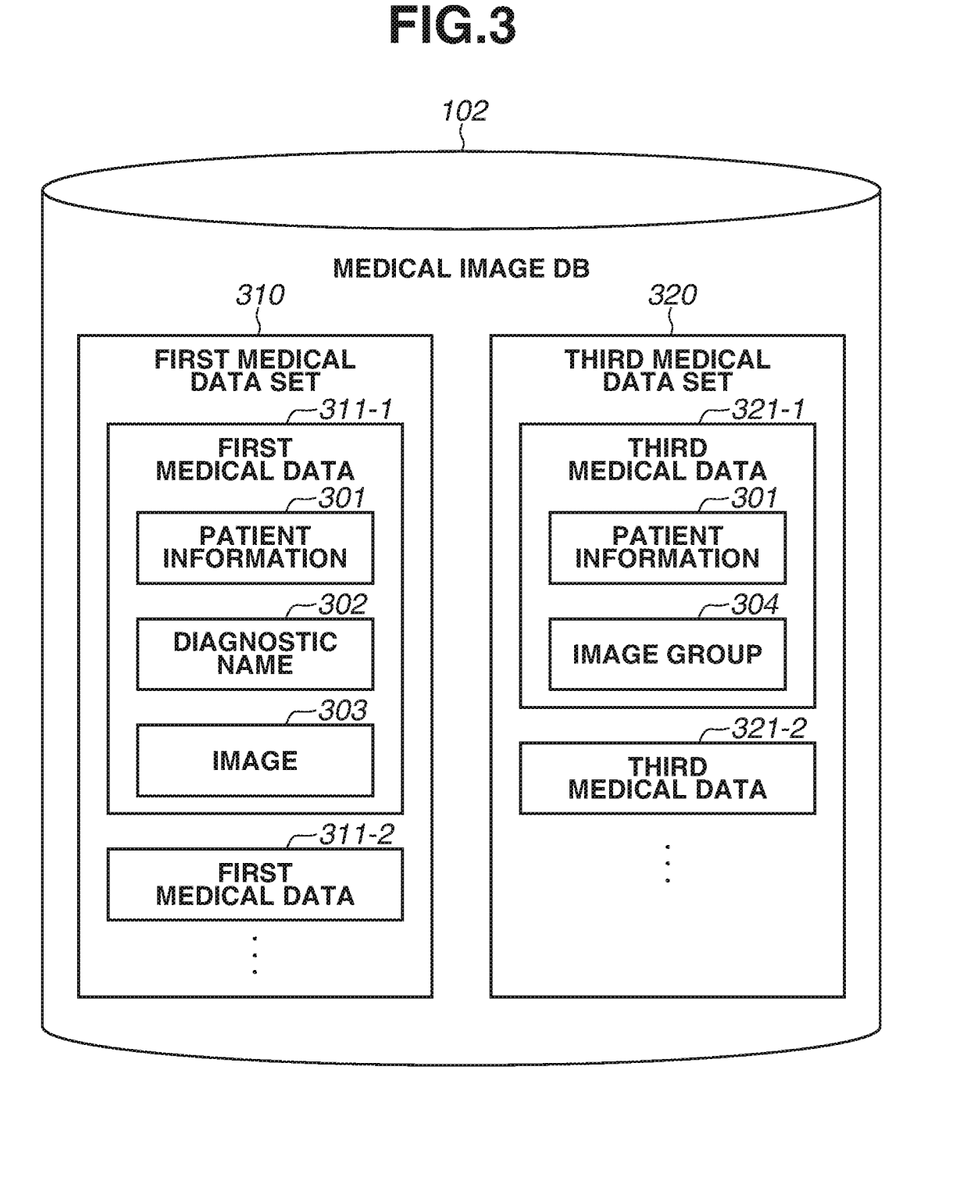
FIG. 3 conceptually illustrates a configuration of a medical image database (DB) according to the first and second exemplary embodiments.

FIG. 3 conceptually illustrates a configuration of medical data to be stored in the medical image DB 102.

Referring to FIG. 3, medical data to be stored in the medical image DB 102 includes a first medical data set 310 and a third medical data set 320. The first medical data set 310 is a medical data set to be used for verification of a classifier. The first medical data set 310 includes a plurality of pieces of first medical data 311-$i$ (i=1, . . . , N1) which includes information such as patient information 301, a diagnostic name 302, and an image 303. The patient information 301 is information about each patient, such as an identifier (ID), name, age, and gender of the patient. The diagnostic name 302 refers to the diagnostic name for an image 303, for example, "Primary", "Metastatic", and "Benign" according to the present exemplary embodiment. "Primary" refers to a primary lung cancer, "Metastatic" refers to a metastatic lung cancer, and "Benign" refers to a benign nodule. The image 303 is a three-dimensional partial region image including a lung nodule extracted from a CT image. The third medical data set 320 is a medical data set to be classified by the information processing apparatus 101 (medical data set subjected to classification). The third medical data set 320 includes a plurality of pieces of third medical data 321-$i$ (i=1, . . . , N3) which includes the patient information 301 and an image group 304. The image group 304 includes images acquired in one image capturing by the CT apparatus, i.e., a plurality of cross section images (hereinafter referred to as slice images).

The diagnostic name 302 may be "Malignant" or "Benign", or may be a diagnostic name derived by subdividing "Primary", "Metastatic", and "Benign". The image 303 may be a combination of a CT image and coordinate information indicating the three-dimensional subregion including a lung nodule. The first medical data 311-$i$ and the third medical data 321-$i$ may include information other than the above-described information.

(Function Blocks)

Figure 4:
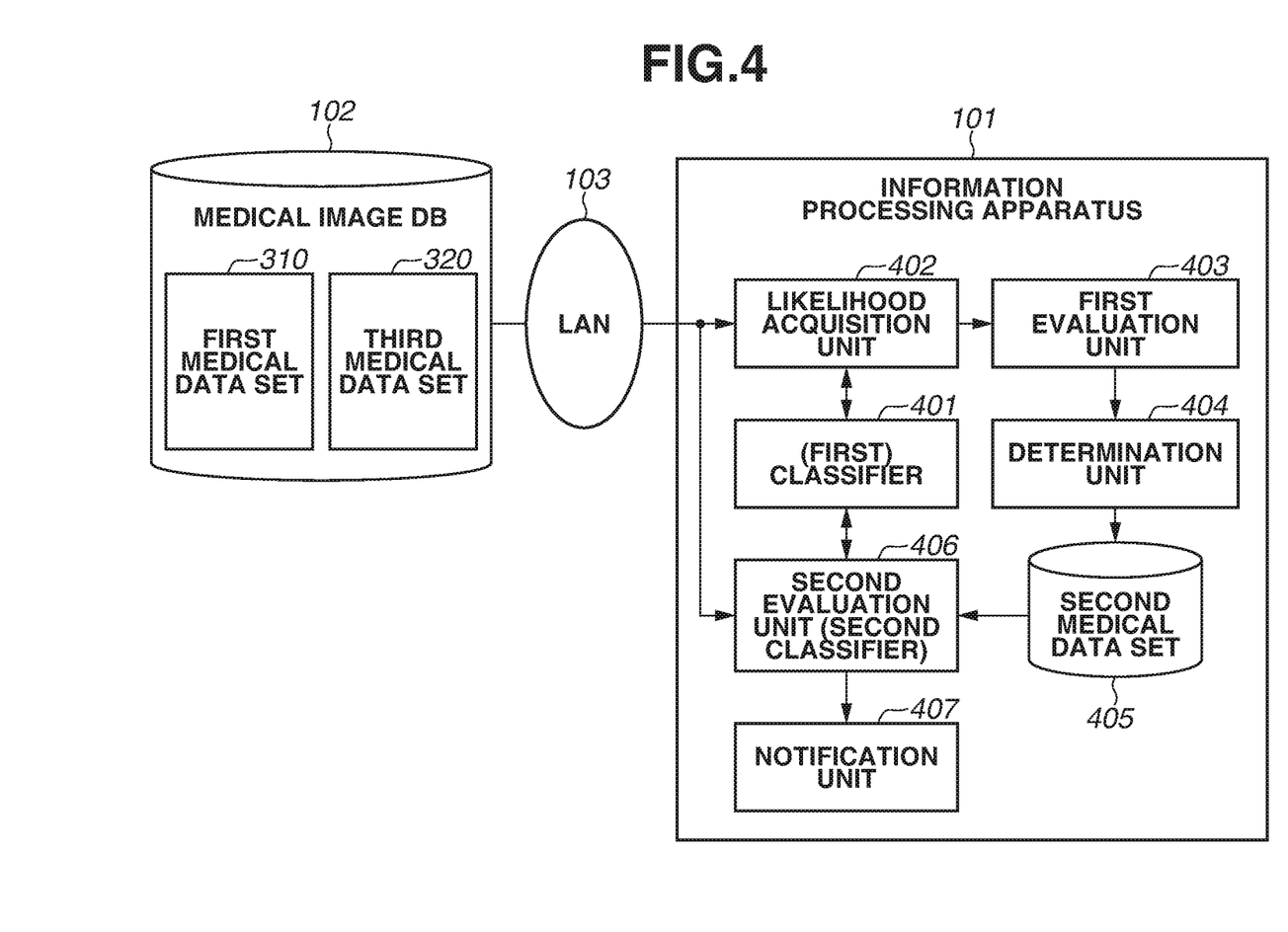
FIG. 4 is a function block diagram illustrating the information processing apparatus according to the first exemplary embodiment.

FIG. 4 is a function block diagram illustrating the information processing apparatus 101 according to the present exemplary embodiment.

Referring to FIG. 4, the information processing apparatus 101 includes a classifier 401 (first classifier) for classifying the diagnostic name, a likelihood acquisition unit 402 for acquiring the likelihood (class likelihood) indicating the presence probability to the class by the classifier 401, and a first evaluation unit 403 for evaluating the deviance between the class likelihood and the correct answer. The information processing apparatus 101 further includes a determination unit 404 for determining whether the deviance satisfies a predetermined criterion, and a second medical data set 405 as a medical data set in which the deviance satisfies the predetermined criterion. The information processing apparatus 101 further includes a second evaluation unit (second classifier) 406 for evaluating the third medical data (medical data subjected to classification) based on the second medical data set 405, and a notification unit 407.

For example, upon input of the subregion image of the lung nodule in the image 303 configuring the first medical data, the classifier 401 (first classifier) performs classification to the diagnostic name (class) corresponding to the image 303. As a result of classifying the diagnostic name, the classifier 401 (first classifier) indicates which class the input image 303 is classified as in terms of the class likelihood. More specifically, as a result of the classification, the classifier 401 outputs the likelihood for "Primary", the likelihood for "Metastatic", and the likelihood for "Benign". More specifically, the classifier 401 is a Convolutional Neural Network (CNN) that has performed machine learning by using a medical data set for learning. More specifically, the class classified by the classifier 401 is a class including the diagnostic name.

The likelihood acquisition unit 402 inputs the image 303 configuring the first medical data set 310 acquired from the medical image DB 102 to the classifier 401 (first classifier) and acquires the class likelihood as a result of the classification by the classifier 401. More specifically, the result of the classification by the classifier 401 is an output from the final layer of the CNN. The likelihood acquisition unit 402 acquires the output values of three nodes corresponding to "Primary", "Metastatic", and "Benign" having undergone a calculation called Softmax.

The first evaluation unit 403 evaluates the degree of deviance between the class likelihood to the class for the first medical data 311-$i$ (i=1, . . . , N1) configuring the first medical data set 310 acquired by the likelihood acquisition unit 402 and the correct answer of the class corresponding to the correct answer label. More specifically, for the class corresponding to the correct answer, the first evaluation unit 403 calculates the absolute value of the difference between the likelihood to the class corresponding to the correct answer label in the result of the classification by the classifier 401 and 1.0. The correct answer label refers to the diagnostic name corresponding to medical data. For the classification of other than the class corresponding to the correct answer label, the first evaluation unit 403 calculates the absolute value of the difference between the class likelihood of the class having the highest likelihood, out of classes other than the class having the class likelihood to the correct answer class and 0.0. The sum of the likelihood difference to the correct answer class and the likelihood difference to the non-correct answer class is considered as the evaluation value. For example, the correct answer of the class when the diagnostic name (correct answer label) is "Primary" is described as (1.0, 0.0, 0.0). A classification result (class likelihood) where the likelihood for "Primary" is 0.8, the likelihood for "Metastatic" is 0.2, and the likelihood for "Benign" is 0.0 is described as (0.8, 0.2, 0.0). When the first evaluation unit 403 evaluates the deviance between the class likelihood (0.8, 0.2, 0.0) and the correct answer (1.0, 0.0, 0.0) based on the classification result, a deviance of |0.8−1.0|+|0.2−0.0|=0.4 results. Likewise, when the class likelihood is (0.8, 0.1, 0.1), the deviance is 0.3. When the class likelihood is (0.6, 0.4, 0.0), the deviance is 0.8. When the class likelihood is (0.6, 0.2, 0.2), the deviance is 0.6. Therefore, even for "Primary" for which the classification result coincides with the correct answer, the deviance increases when the likelihood for "Primary" is low, and the highest likelihood for other than "Primary" is high. Likewise, when the class likelihood is (0.3, 0.7, 0.0), the deviance is 1.4. When the class likelihood is (0.3, 0.35, 0.35), the deviance is 1.05. When the class likelihood is (0.1, 0.9, 0.0), the deviance is 1.8. When the class likelihood is (0.1, 0.45, 0.45), the deviance is 1.35. Therefore, even if the classification result (class likelihood) is different from the correct answer ("Primary"), the deviance decreases when the likelihood for "Primary" is high, and the highest likelihood for other than "Primary" is low. More specifically, the deviance evaluated by the present exemplary embodiment is different from the simple accuracy rate and the likelihood for the classification as the correct answer. The deviance is acquired by totally evaluating the degree of correct answer and the degree of the non-correct answer. More specifically, the first evaluation unit 403 evaluates the degree of deviance based on the likelihood to the class corresponding to the correct answer label and the likelihood to a class not corresponding to the correct answer label, out of the class likelihood. For example, the evaluation value obtained by the first evaluation unit 403 is not limited only to that obtained in the present exemplary embodiment. For example, the total of the absolute value of the difference between the class likelihood to the class corresponding to the correct answer label by the classifier 401 and 1.0 and the difference between the likelihood of a class other than the class corresponding to the correct answer label and 0.0 may be calculated as the evaluation value. More specifically, the form of the evaluation value calculated by the first evaluation unit 403 does not matter as long as the deviance between the correct answer and the classification result by the classifier 401 can be determined.

The determination unit 404 determines whether a predetermined criterion is satisfied from the first medical data 311-$i$ (i=1, . . . , N1) of the first medical data set 310 based on the evaluation result (evaluation value) of the first evaluation unit 403. Medical data exceeding the predetermined criterion is considered as the second medical data set 405. The predetermined criterion is a predefined fixed value. For example, the value of the deviance is 1.2 or larger. In this case, data having class likelihood of (0.3, 0.35, 0.35) and (0.25, 0.375, 0.375) provides deviances of 1.05 and 1.125, respectively. Therefore, even data having the correct answer "Primary" and a different classification result (class likelihood) is not considered as the second medical data satisfying the predetermined criterion. On the contrary, data having class likelihood of (0.3, 0.5, 0.2) provides a deviance of 1.2, and data having class likelihood of (0.25, 0.45, 0.3) also provides a deviance of 1.2. Both data satisfies the predetermined criterion. Therefore, based on the first medical data set 310, the data of the first medical data set 310 is considered as the second medical data set 405 which is a data set determined to satisfying the predetermined criterion by the first evaluation unit 403. A setting unit (not illustrated) for setting a predetermined criterion may be separately provided, or the user may receive an input of a predetermined reference value via a Graphical User Interface (GUI).

The second evaluation unit (second classifier) 406 evaluates the similarity between image data configuring the second medical data set 405 and image data of the subregion of the lung nodule extracted from the series image 304 of the third medical data set 320. More specifically, the second evaluation unit (second classifier) 406 evaluates the similarity between the second medical data and the third medical data. According to the present configuration, the similarity to the second medical data decreases, if the classifier 401 has learned the features to be classified, for the third medical data as medical data to be subjected to classification. On the other hand, if the classifier 401 has not learned the features to be classified, the similarity to the second medical data increases. This means that evaluating the similarity makes it possible to determine whether the classifier 401 has learned the features to be classified.

Figure 5:
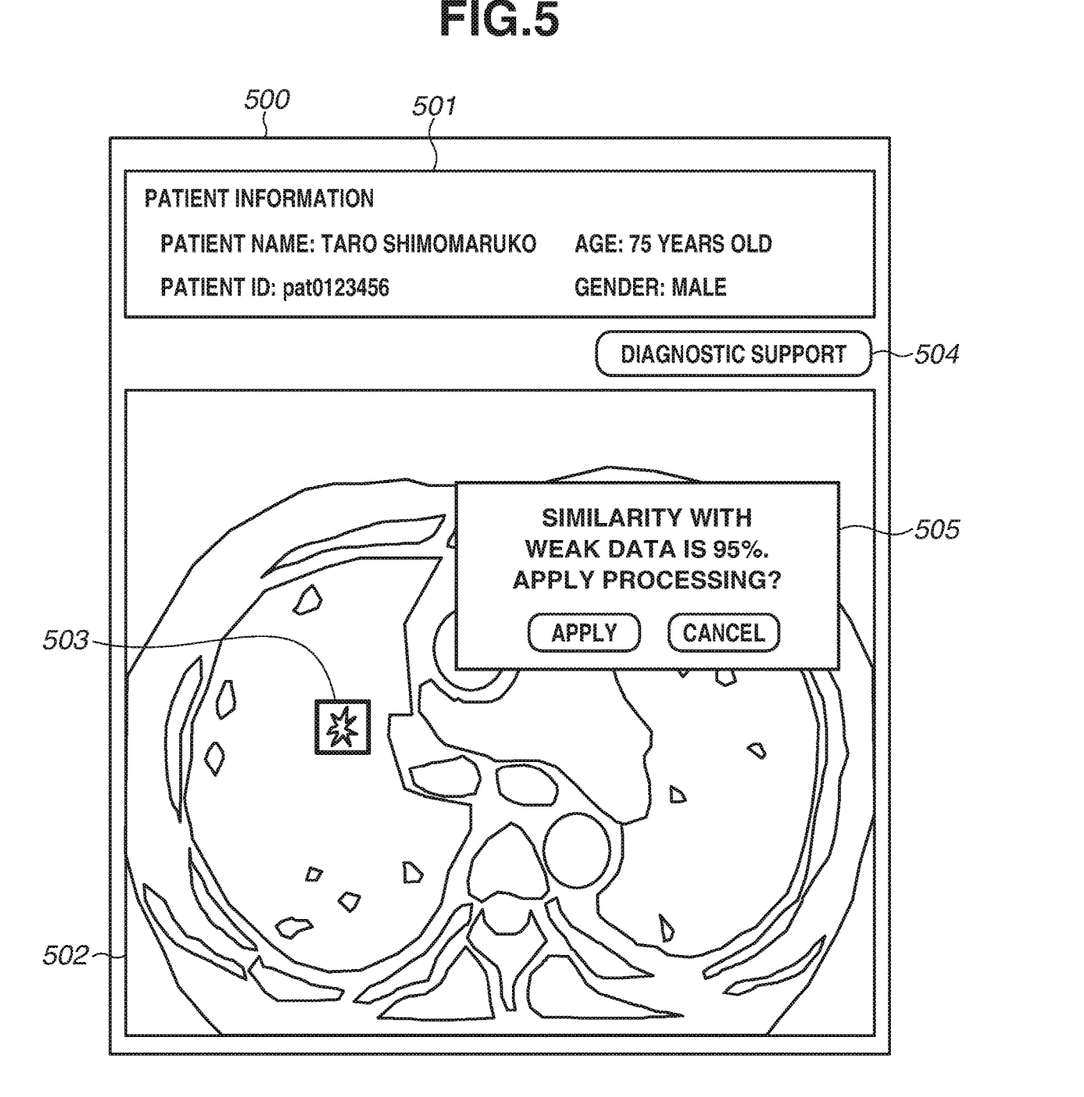
FIG. 5 illustrates an example of a display screen of the information processing apparatus according to the first exemplary embodiment.

A subregion image of the lung nodule is extracted based on an operation on the display screen illustrated in FIG. 5. The similarity is evaluated by a classifier generated based on teacher data given a label (class) indicating whether the data of the first medical data set 310 is the data of the second medical data set 405. The teacher data is a data set for binary classification given a label indicating the second medical data set 405 and a label indicating other medical data, out of the first medical data set 310. More specifically, for the image 303 configuring the first medical data set 310, the second evaluation unit 406 evaluates the similarity by using the second classifier that has completed machine learning based on teacher data given a label (class) indicating whether the data of the first medical data set 310 is the data of the second medical data set 405. The second classifier is, for example, a CNN. The likelihood corresponding to the label indicating the second medical data set 405 output from the CNN is considered as the similarity (hereinafter referred to as a similarity). More specifically, the second evaluation unit 406 performs evaluation based on the second classifier for calculating the likelihood for classifying by using a class whether to be data of the second medical data set 405.

The notification unit 407 notifies the user of information based on the evaluation result by the second evaluation unit 406. More specifically, the notification unit 407 displays the similarity to the data of the second medical data set 405 on the display screen. The display screen will be described below with reference to FIG. 5.

More specifically, the information processing apparatus 101 according to the present exemplary embodiment includes a likelihood acquisition unit 402 for acquiring the class likelihood for the first medical data given a correct answer label by using the first classifier 401 for classifying medical data. The information processing apparatus 101 further includes the first evaluation unit 403 for evaluating the degree of deviance based on the class likelihood acquired by the likelihood acquisition unit 402 and the class answer of the class corresponding to the correct answer label. The information processing apparatus 101 further includes the determination unit 404 for determining whether the degree of deviance by the first evaluation unit 403 satisfies a predetermined criterion. The information processing apparatus 101 further includes the second evaluation unit 406 for evaluating the similarity between the second medical data set 405 and the third medical data set 320 to be subjected to classification, based on the second medical data set 405 satisfying the predetermined criterion, out of the first medical data.

(Display Screen)

FIG. 5 illustrates an example of a display screen of the information processing apparatus 101 according to the present exemplary embodiment.

Referring to FIG. 5, a display screen 500 is a user interface screen displayed on the display 207. The display screen 500 includes a patient information display area 501, an image display area 502, and a diagnostic support button 504. Referring to FIG. 5, the display screen 500 includes a lung nodule subregion 503 and a notification area 505 displayed by the notification unit 407.

The patient information display area 501 displays information about patient information 301 of the third medical data 321-$i$ (i=1, . . . , N3). FIG. 5 illustrates a display example when the patient name is "Taro Shimomaruko", the patient ID is "pat0123456", the age is "75 years old", and the gender is "male".

The image display area 502 displays the series image 304 of the third medical data 321-$i$ (i=1, . . . , N3). In the image display area 502, the user can perform a slice feed of the series image 304 to be displayed, and change gradation display conditions called Window Level (WL)/Window Width (WW).

The lung nodule subregion 503 is specified, for example, when the user performs a mouse drag operation in the image display area 502 and canceled when the user clicks the mouse button. According to the drag operation, the lung nodule subregion 503 is displayed on the slice image, and a three-dimension area (cube) having the same depth is specified centering on the displayed slice image. The specification of a subregion is not limited to a specification through a user operation. For example, a subregion may be specified with another image procession unit, or specified by using a model based on machine learning designed to extract a subregion from the image area.

The diagnostic support button 504 is a button for classifying the diagnostic name based on the image of the lung nodule subregion 503. When the user clicks the diagnostic support button 504 with the mouse, the information processing apparatus 101 extracts the image of the lung nodule subregion 503 and then classifies the diagnostic name based on the extracted image.

The notification area 505 displays information based on the similarity between the image of the lung nodule subregion 503 and the image of the second medical data set 405. More specifically, for example, the notification area 505 is a pop-up window which displays the similarity and includes a method for specifying whether to apply or cancel processing. More specifically, the notification unit 407 notifies the user of the similarity.

(Processing Flow)

Figure 6:
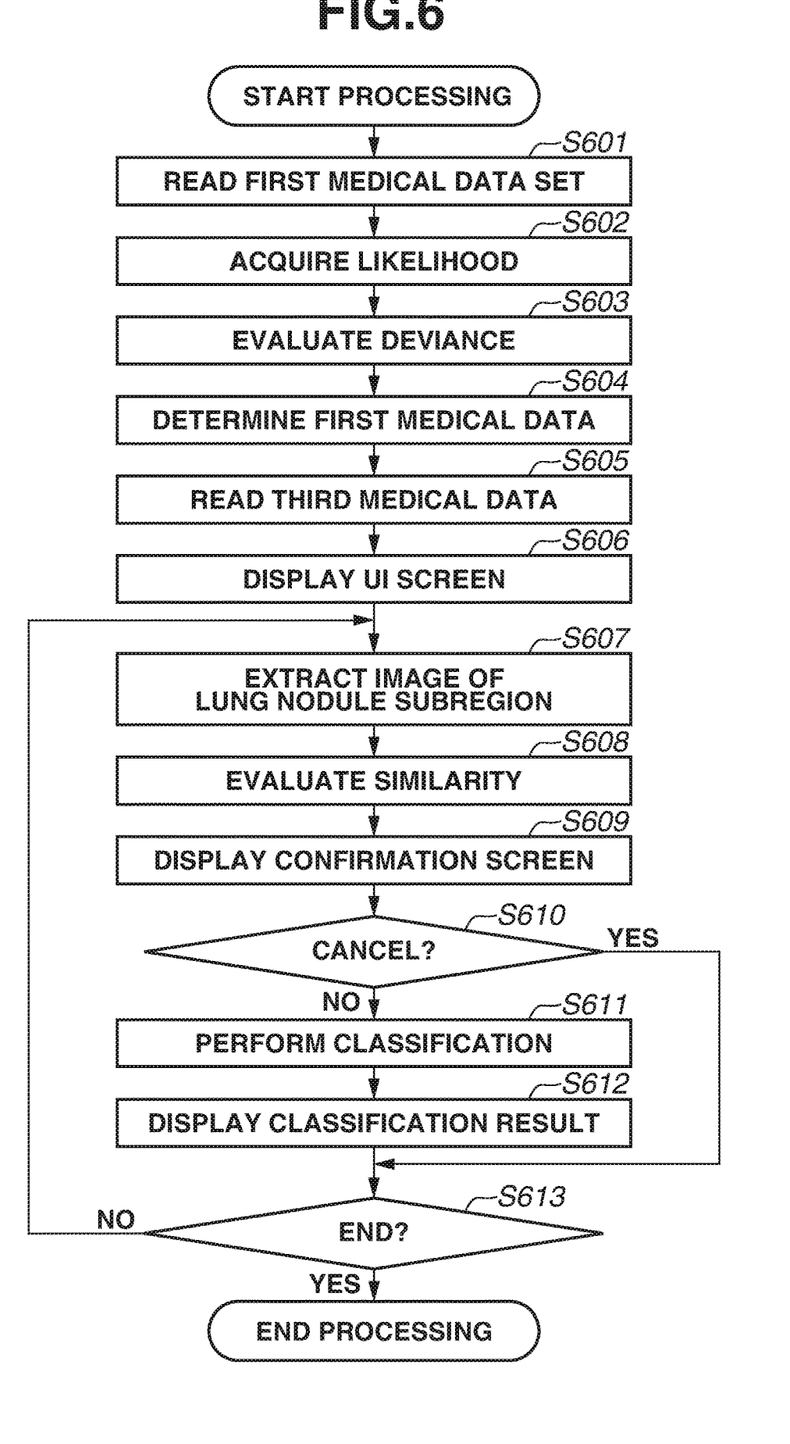
FIG. 6 is a flowchart illustrating processing of the information processing apparatus according to the first exemplary embodiment.

FIG. 6 is a flowchart illustrating processing for notifying the user of the result of the medical data classification for the information processing apparatus 101 according to the present exemplary embodiment.

This processing is performed based on an instruction from the user after the activation of the information processing apparatus 101. When the user specifies the execution of processing, the user specifies the third medical data 321-$i$ (i=1, . . . , N3) to be subjected to processing (medical data to be subjected to classification).

In step S601, the likelihood acquisition unit 402 reads specified first medical data set 310 from the medical image DB 102.

In step S602, the likelihood acquisition unit 402 inputs the image 303 configuring the first medical data set 310 read in step S601 to the classifier 401, and acquires the likelihood of the classification to classes as a classification result from the classifier 401.

In step S603, the first evaluation unit 403 evaluates the degree of deviance between the likelihood of the classification to classes and the correct answer based on the likelihood of the classification to classes acquired by the likelihood acquisition unit 402 and the diagnostic name 302 of the first medical data set 310.

In step S604, the determination unit 404 determines the first medical data 311-$i$ (i=1, . . . , N1) of the first medical data set 310 based on the degree of deviance evaluated by the first evaluation unit 403 and a predetermined criterion. The predetermined criterion is, for example, a predefined fixed value. More specifically, medical data where the degree of deviance from the first medical data satisfies a predetermined criterion is considered as the second medical data set 405. On the other hand, medical data where the degree of deviance is less than the predetermined criterion is not considered as the second medical data set 405.

In step S605, a user interface control unit (CPU 203) reads the third medical data 321-$i$ (i=1, . . . , N3) specified when the present processing is executed. In step S606, the user interface control unit (CPU 203) displays an example of the display screen 500 illustrated in FIG. 5. In step 607, the image of the lung nodule subregion 503 specified based on a user operation is extracted.

In step S608, the second evaluation unit 406 evaluates the similarity between the image extracted in step S607 and the image of the second medical data set 405. The second evaluation unit 406 evaluates the similarity by using a binary classification model (second classifier) that has completed machine learning based on teacher data given a label indicating whether the data of the first medical data set 310 is the data of the second medical data 405, out of the first medical data.

In step S609, the notification unit 407 displays the notification area 505 on the display screen 500 based on the evaluation result in step S608. The notification area 505 may be displayed by the notification unit 407 only when the evaluation result in step S608 exceeds a predetermined value.

In step S610, the user interface control unit (CPU 203) determines whether the cancel button in the notification area 505 is clicked. When the cancel button is clicked (YES in step S610), the processing proceeds to step S613. On the other hand, when the apply button is clicked instead of the cancel button (NO in step S610), the processing proceeds to step S611. In step S611, the information processing apparatus 101 further classifies the image extracted in step S607 by using the classifier 401, and displays the result of the classification on the display screen 500. In step S613, the user interface control unit (CPU 203) determines whether an end operation is performed. When the end operation is not performed (NO in step S613), the processing returns to step S607. On the other hand, when the end operation is performed (YES in step S613), the processing exits the flowchart.

As described above, according to the present exemplary embodiment, the information processing apparatus 101 evaluates, via the first evaluation unit 403, the degree of deviance between the likelihood of the classification by the classifier 401 and the correct answer. Then, the determination unit 404 determines whether the criterion is satisfied based on the degree of deviance, and then the second medical data set 405 is acquired. Then, the second evaluation unit 406 evaluates the similarity to the third medical data as medical data to be subjected to classification. The information processing apparatus 101 notifies the user of the result of the evaluation via the notification unit 407. This configuration enables the user to recognize whether the classifier has not sufficiently learned data for the image subjected to classification. The user can select whether to continue the processing based on the notification. Thus, if the processing target data is weak data for the classifier 401, the user can recognize in advance that the result of the classification by the classifier 401 has low reliability. If the user presumes that the result of the classification has low reliability, the user can select the cancellation of the classification processing in advance. The configuration in steps S601 to S604 is a process for generating the second classifier for classifying whether the classification target data is the data of the second medical data set 405. Therefore, when using a classifier that has completed learning or using a classifier separately generated by performing the processing by another information processing apparatus, the processing may be performed from step S605.

(First Modification of First Exemplary Embodiment)

The first evaluation unit 403 according to the first exemplary embodiment calculates the deviance between the classification result by the classifier 401 and the correct answer. For the class corresponding to the correct answer class, the first evaluation unit 403 calculates the absolute value of the difference between the class likelihood to the class corresponding to the correct answer label and 1.0. For the classification to non-correct answer classes, the first evaluation unit 403 calculates the absolute value of the difference between the class likelihood of the class having the highest likelihood, out of non-correct answer classes, and 0.0. The first evaluation unit 403 performs evaluation by calculating the sum of the likelihood difference to the correct answer class and the likelihood difference to the non-correct answer class. On the other hand, the first evaluation unit 403 according to the first modification of the first exemplary embodiment evaluates the degree of deviance (calculates the evaluation value) by subtracting the class likelihood of the class having the highest likelihood, out of non-correct answer classes, from the class likelihood corresponding to the correct answer class. When applying the method for calculating this evaluation value, the smallest deviance value is 1.0 and the largest deviance value is −1.0, out of the evaluation values calculated by the first evaluation unit 403. As an example of a predetermined criterion, in the case where the deviance value is −0.2 or less, the determination unit 404 determines that the data of the first medical data set 310 is the data of the second medical data set 405.

The first evaluation unit 403 may determine the predetermined criterion based on the number of classifications. More specifically, the determination unit 404 determines whether the data of the first medical data set 310 is the data of the second medical data set 405 by determining how much the deviance value is less than the reciprocal of the number of classifications. In an example case where the number of classifications is 3, when the deviance value is equal to or less than 0.3135 which is about 5 percent lower than $1/3 = 0.33...$, the determination unit 404 determines that the data of the first medical data set 310 is the data of the second medical data set 405. The present modification enables performing evaluation in consideration of the number of classes to be subjected to classification.

(Second Modification of First Exemplary Embodiment)

Figure 7A:
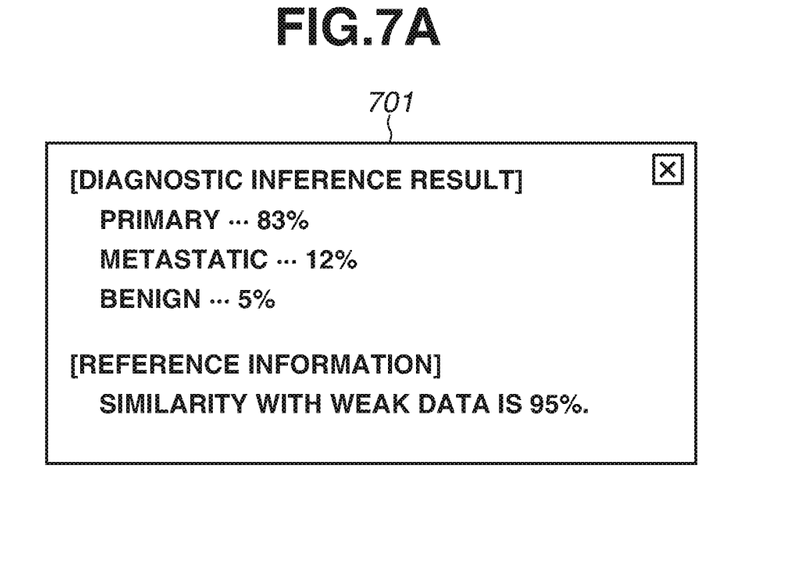
FIGS. 7A and 7B illustrate examples of display screens of an information processing apparatus according to a second modification of the first exemplary embodiment
Figure 7B:
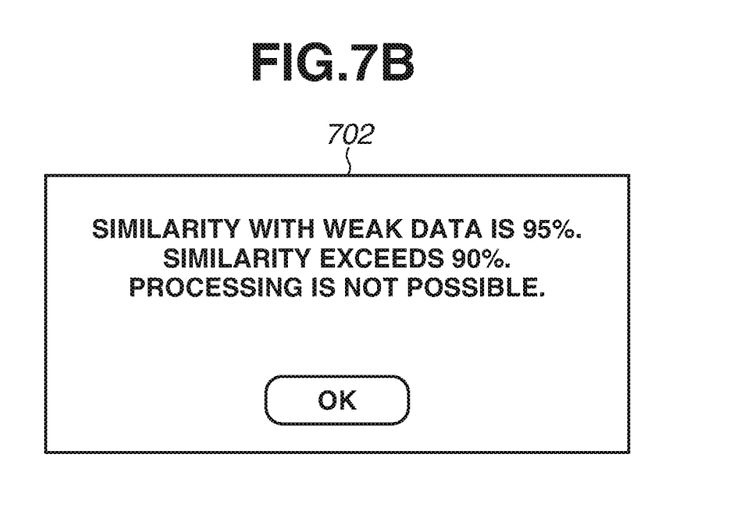

According to the first exemplary embodiment, the notification unit 407 displays the notification area 505 before starting the classification processing and prompts the user to select the apply or cancel button. However, the similarity may be displayed together with the classification result after the classification processing, as illustrated in FIG. 7A. When the similarity exceeds a predetermined value, as illustrated in FIG. 7B, the second evaluation unit 406 may control so as not to perform the classification processing by the classifier 401 (first classifier), and the notification unit 407 may display the failure to perform the processing together with the similarity. More specifically, based on the similarity, the second evaluation unit 406 determines whether to use the third medical data as input data to the first classifier.

FIG. 7A illustrates an example of a notification area 701 according to the present modification. The notification area 701 displays the classification result (the likelihood for "Primary" is 83%, the likelihood for "Metastatic" is 12%, and the likelihood for "Benign" is 5%), and the 95% similarity to the second medical data set 405 ("Weak Data" in the screen example).

FIG. 7B illustrates an example of a notification area 702 according to the present modification. The notification area 702 displays the failure to perform the classification processing since the similarity to the second medical data set 405 ("Weak Data" in the screen example) is 95% which exceeds 90%, and also displays a confirmation (OK) button. After a certain period of time has elapsed, the window of the notification area 702 may automatically close without displaying the confirmation (OK) button.

According to the present modification, when the similarity exceeds a predetermined value, the user does not need to perform an operation for applying or canceling the processing.

Like the first exemplary embodiment, a second exemplary embodiment will be described below centering on an information processing apparatus as a CAD system for performing diagnostic inference related to a lung nodule shadow on a chest X-ray CT image.

Figure 8:
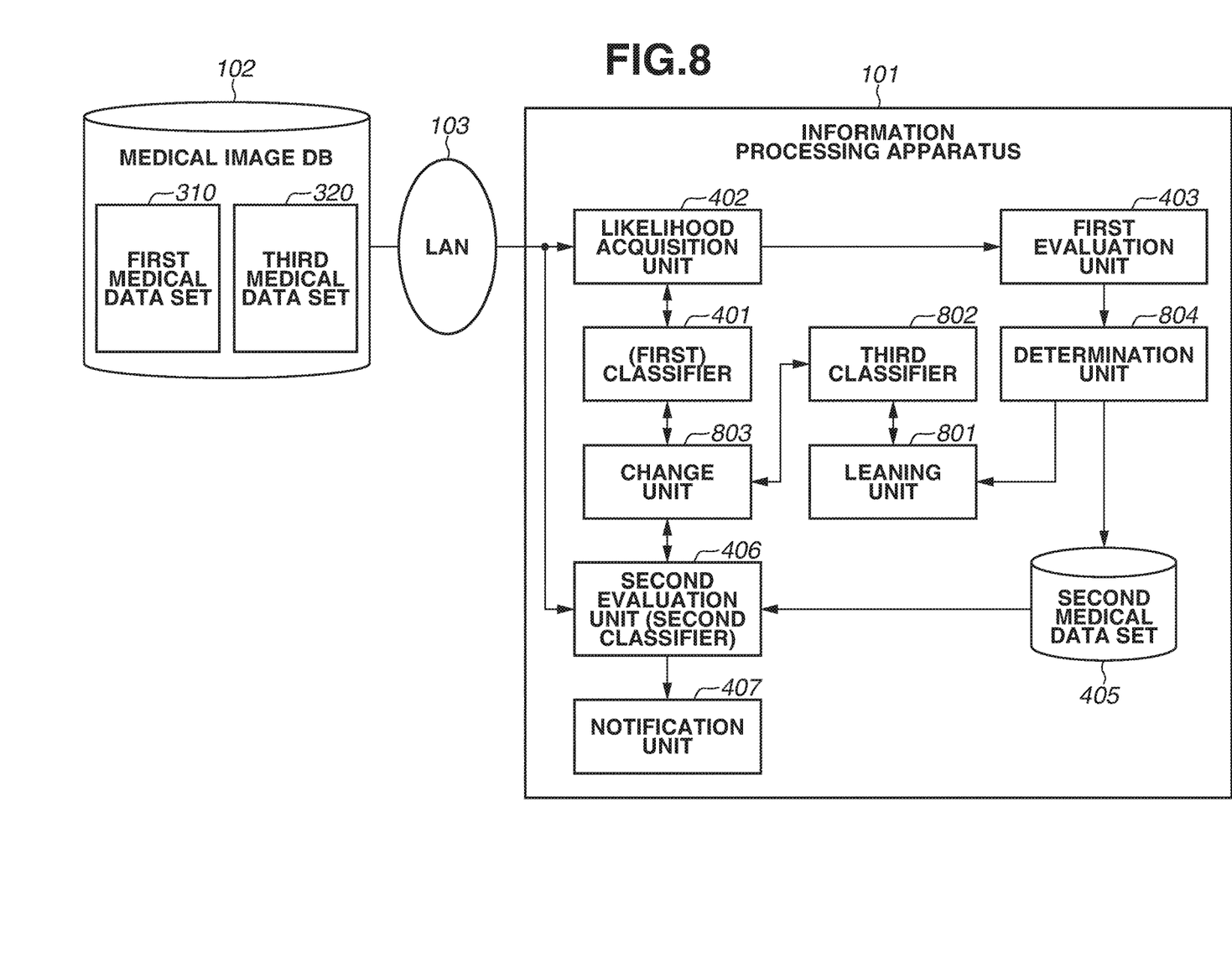
FIG. 8 is a function block diagram illustrating the information processing apparatus according to a second exemplary embodiment.

According to the first exemplary embodiment, the determination unit 404 evaluates the degree of deviance between the class likelihood by a classifier and the correct answer. Then, based on the degree of deviance, the second evaluation unit 406 evaluates the similarity between medical data satisfying a predetermined criterion (second medical data set 405) and the processing target data (third medical data set 320), and the user is notified of the result. The present exemplary embodiment performs the classification processing by using a third classifier 802 different from the classifier

401 based on the determination result by a determination unit 804. The third classifier 802 is a classifier based on machine learning. The information processing apparatus 101 according to the present exemplary embodiment performs the classification processing by switching between the classifier 401 (hereinafter referred to as a first classifier) and the third classifier 802 based on the evaluation result by the second evaluation unit 406.

The system configuration and the hardware configuration of the information processing apparatus, and the configuration of the medical image DB 102 according to the present exemplary embodiment are similar to those according to the first exemplary embodiment, and redundant descriptions will be omitted.

FIG. 8 is a function block diagram illustrating the information processing apparatus according to the present exemplary embodiment. Referring to FIG. 8, the information processing apparatus 101 includes a learning unit 801, a third classifier 802, and a change unit 803.

For the image 303 determined to be the data of the second medical data set 405 by the determination unit 804, out of the first medical data set 310, the learning unit 801 generates a third classifier based on machine learning by using the diagnostic name 302 as a correct answer label (class). More specifically, the information processing apparatus 101 includes the third classifier 802 for performing classification based on teacher data having a label of the diagnostic name in the second medical data set 405.

The change unit 803 switches the classifier for classifying the image extracted from the third medical data set 320 between the first classifier 401 and the third classifier 802, based on the evaluation result by the second evaluation unit 406. More specifically, when the similarity between the third medical data and the data of the second medical data set 405 satisfies a predetermined criterion (e.g., 0.5 or larger), the change unit 803 selects the third classifier 802. On the other hand, when the similarity does not satisfy the predetermined criterion, the change unit 803 selects the first classifier 401. More specifically, the second evaluation unit 406 determines whether the third medical data is used as input data to the third classifier 802 based on the similarity. The information processing apparatus 101 further includes the change unit 803 for changing the classifier for inputting the third medical data, based on the similarity acquired by the second evaluation unit 406.

Figure 9:
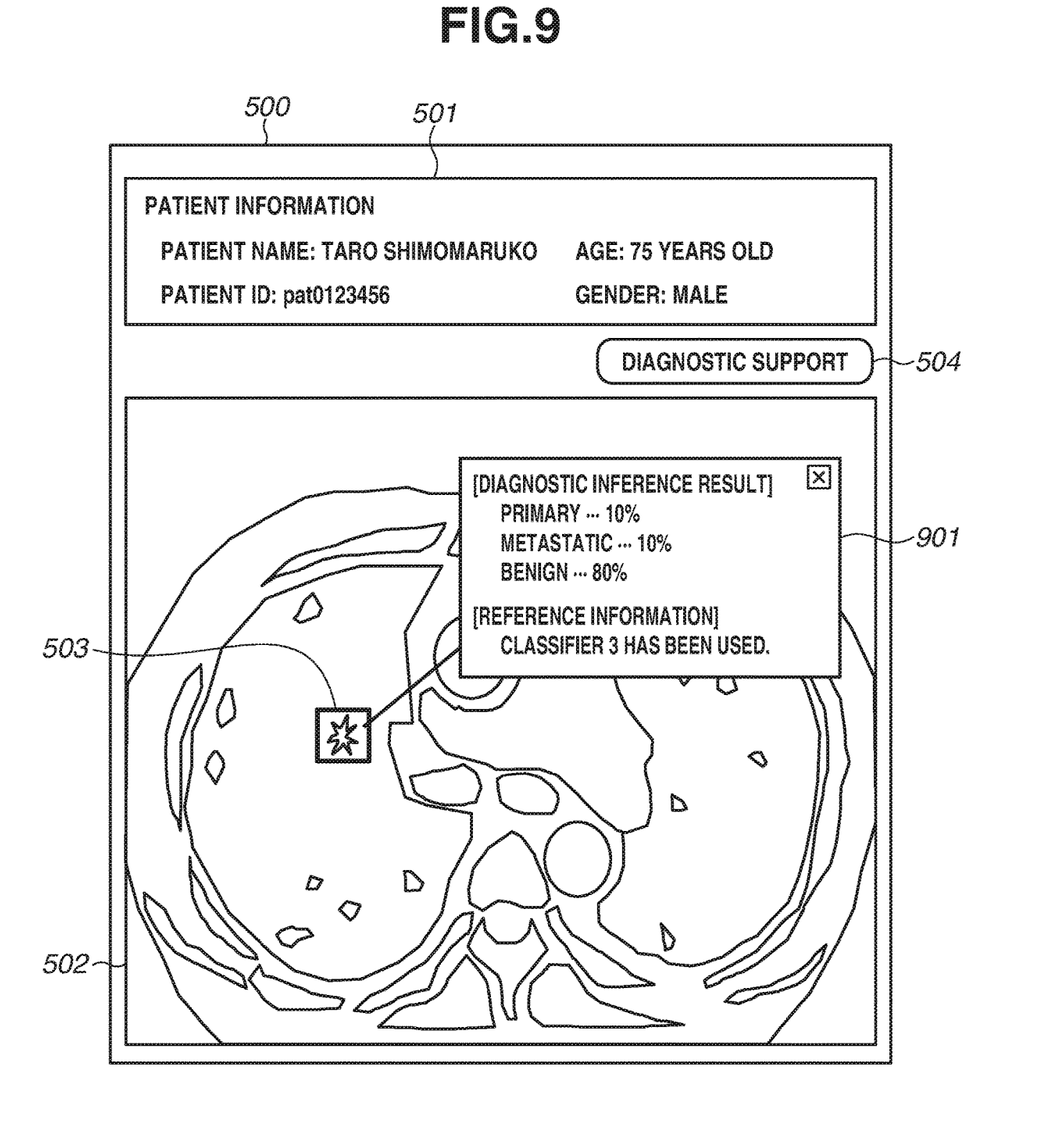
FIG. 9 illustrates an example of a display screen of the information processing apparatus according to the second exemplary embodiment.

FIG. 9 is an example of a display screen of the information processing apparatus according to the present exemplary embodiment.

Referring to FIG. 9, a notification area 901 is an example of a notification area by the notification unit 407. The notification area 901 according to the present exemplary embodiment displays a notification that the third classifier ("classifier 3" in the example display screen) has been used together with the classification result by the classifier. More specifically, the notification unit 407 notifies the user of the classifier that has classified the third medical data (medical data to be subjected to classification).

Figure 10:
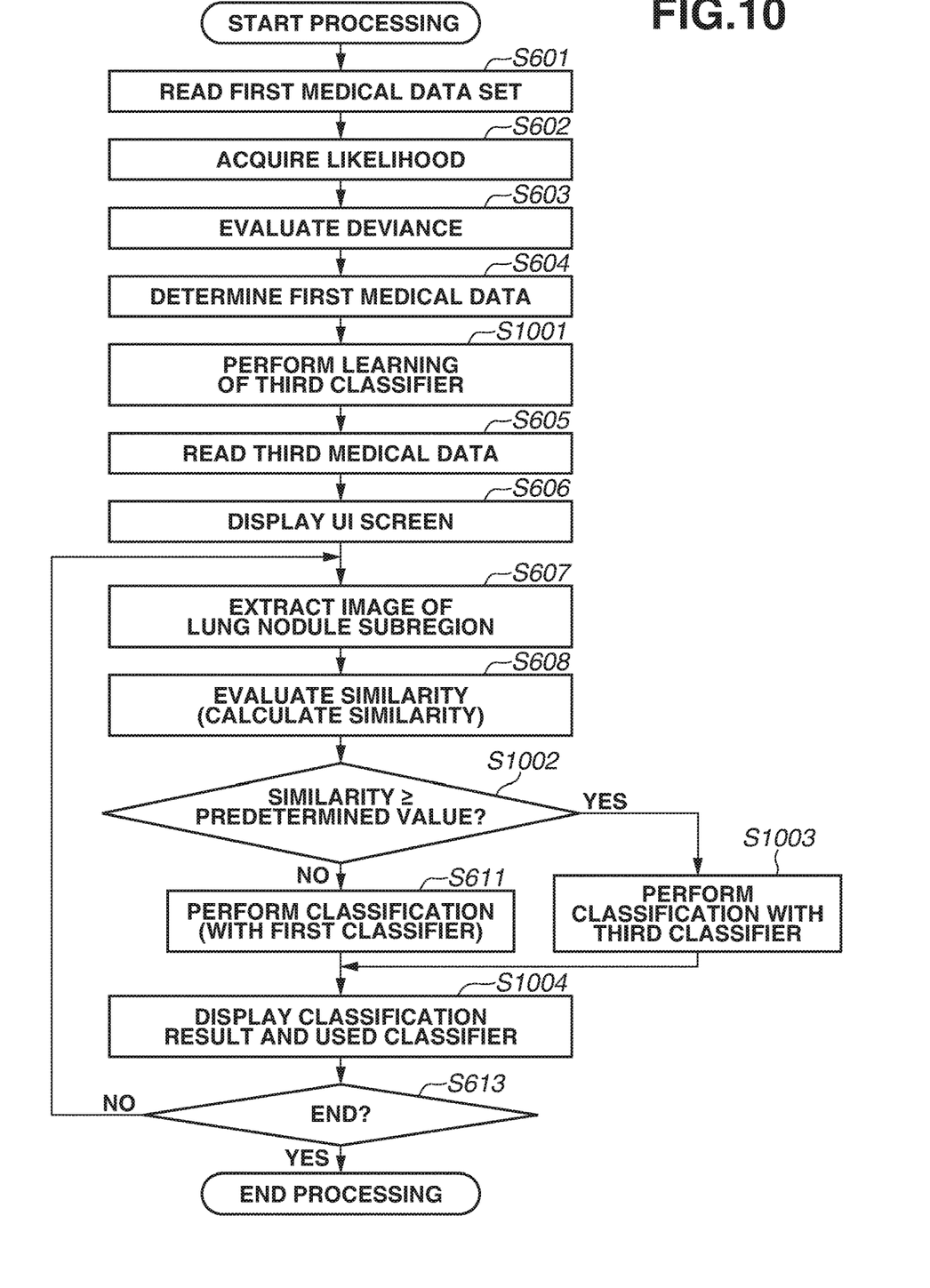
FIG. 10 is a flowchart illustrating processing of the information processing apparatus according to the second exemplary embodiment.

FIG. 10 is a flowchart illustrating processing of the information processing apparatus according to the present exemplary embodiment.

According to the present exemplary embodiment, following step S604, the processing proceeds to step S1001. In step S1001, the learning unit 801 performs machine learning of the third classifier 802 for classifying the diagnostic name 302 by using teacher data determined to be the data of the second medical data set 405, based on the determination result by the determination unit 804.

In step S1002 following step S608, the change unit 803 evaluates whether the similarity calculated in step S608 is equal to or larger than a predetermined value. When the similarity is equal to or larger than the predetermined value (YES in step S1002), the processing proceeds to step S1003. In step S1003, the information processing apparatus 101 classifies the image extracted by using the third classifier 802 in step S607. On the other hand, when the similarity is less than the predetermined value (NO in step S1002), the processing proceeds to step S611. In step S611, the information processing apparatus 101 classifies the extracted image by using the first classifier 401.

In step S1004, the notification unit 407 displays the used classifier in the notification area 901 on the display screen 500.

As discussed above, according to the present exemplary embodiment, the information processing apparatus 101 performs machine learning of the third classifier 802 different from the first classifier 401 based on the determination result by the determination unit 804. The information processing apparatus 101 performs the classification processing by switching between the first classifier 401 and the third classifier 802, based on the evaluation result by the second evaluation unit 406. This makes it possible to suitably evaluate data not having been learned by the classifier and separately classify weak data for the first classifier 401 by using the third classifier 802. Thus, the improvement in the classification accuracy can be expected.

(First Modification of Second Exemplary Embodiment)

The learning unit 801 according to the second exemplary embodiment performs machine learning of the third classifier 802 by using, as a correct answer label, the diagnostic name 302 of the data determined to be the data of the second medical data set 405 by the determination unit 804, out of the first medical data set 310. According to the present modification, the learning unit 801 performs machine learning of the third classifier 802 by using, as a correct answer label, the diagnostic name 302 of the data of which the similarity as the evaluation result by the second evaluation unit 406 exceeds a predetermined value, out of the first medical data set 310.

According to the present modification, data determined to have a low similarity by the second evaluation unit 406, out of data determined to be the data of the second medical data set 405 by the determination unit 804, is not used for the learning of the third classifier 802. Data determined to have a low similarity by the second evaluation unit 406 is not classified by the third classifier 802 through the change unit 803, and therefore becomes noise for the third classifier 802. By excluding such data from the teacher data, the improvement in the accuracy of the second classifier 802 can be expected.

Other Embodiments

Embodiment(s) of the disclosure can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the disclosure has been described with reference to exemplary embodiments, it is to be understood that the disclosure is not limited to the disclosed exemplary embodiments. The scope of the following claims is to be accorded the broadest interpretation so as to encompass all such modifications and equivalent structures and functions.

This application claims the benefit of Japanese Patent Application No. 2019-132264, filed Jul. 17, 2019, which is hereby incorporated by reference herein in its entirety.

What is claimed is:

1. An information processing apparatus comprising:
a memory storing a program; and
one or more processors which, by executing the program, function as:
 a likelihood acquisition unit configured to acquire class likelihood for first medical data given a correct answer label, by inference processing using a first classifier for classifying medical data;
 a first evaluation unit configured to evaluates a degree of deviance based on the class likelihood acquired by the likelihood acquisition unit and a class answer corresponding to the correct answer label;
 a determination unit configured to determine whether the degree of deviance by the first evaluation unit satisfies a predetermined criterion; and
 a second evaluation unit configured to acquire, from the first medical data, second medical data which is determined to satisfy the predetermined criterion, and evaluate a similarity of third medical data to be subjected to classification with the second medical data,
 wherein the second evaluation unit evaluates the similarity using machine learning and based on teacher data given a label corresponding to information indicating whether the data of the first medical data is the data of the second medical data, and
 wherein the first, second, and third medical data are accessed from a database organized in a storage.

2. The information processing apparatus according to claim 1, wherein the second evaluation unit evaluates the similarity based on a second classifier for classifying whether a classification target is the second medical data.

3. The information processing apparatus according to claim 1, wherein the one or more processors which, by executing the program, further function as a notification unit configured to issue a notification based on an evaluation result by the second evaluation unit.

4. The information processing apparatus according to claim 1, wherein the one or more processors which, by executing the program, further function as a third classifier configured to perform classification based on teacher data given a diagnostic name in the second medical data as a correct answer label.

5. The information processing apparatus according to claim 4, wherein, based on the similarity, the second evaluation unit determines whether the third medical data to be subjected to classification is considered as input data to the third classifier.

6. The information processing apparatus according to claim 1, wherein, based on the similarity, the second evaluation unit determines whether the third medical data to be subjected to classification is considered as input data to the first classifier.

7. The information processing apparatus according to claim 4, wherein the one or more processors which, by executing the program, further function as a change unit configured to change the first classifier or the third classifier for inputting the third medical data to be subjected to classification based on the similarity.

8. The information processing apparatus according to claim 1, wherein the class for the first classifier is a class including a diagnostic name.

9. The information processing apparatus according to claim 3, wherein the notification unit notifies a classifier that has classified the medical data to be subjected to classification.

10. The information processing apparatus according to claim 3, wherein the notification unit notifies the similarity.

11. The information processing apparatus according to claim 1, wherein the first evaluation unit evaluates the degree of deviance based on likelihood of the class corresponding to the correct answer label and likelihood of a class not corresponding to the correct answer label, out of the class likelihood.

12. The information processing apparatus according to claim 4, wherein the one or more processors which, by executing the program, further function as a specification unit configured to specify whether the third medical data to be subjected to classification is to be classified by the third classifier.

13. The information processing apparatus according to claim 1, wherein the predetermined criterion is a criterion for determining whether the first classifier has sufficiently learned.

14. The information processing apparatus according to claim 13, wherein a second evaluation unit acquires the first medical data as the second medical data when it is determined that the first classifier has not sufficiently learned.

15. An information processing method comprising:
acquiring, as likelihood acquisition, class likelihood for first medical data given a correct answer label, by inference processing using a first classifier for classifying medical data;
evaluating, as first evaluation, a degree of deviance based on the class likelihood acquired by the likelihood acquisition and a class answer corresponding to the correct answer label;
determining whether the degree of deviance by the first evaluation satisfies a predetermined criterion; and
acquiring, from the first medical data, second medical data which is determined to satisfy the predetermined criterion, and evaluating, as second evaluation, a similarity of third medical data to be subjected to classification with the second medical data,
 wherein evaluating as the second evaluation comprises evaluating the similarity using machine learning and based on teacher data given a label corresponding to information indicating whether the data of the first medical data is the data of the second medical data, and wherein the first, second, and third medical data are accessed from a database organized in a storage.

16. A non-transitory storage medium storing a program for causing a computer to execute information processing method comprising:

acquiring, as likelihood acquisition, class likelihood for first medical data given a correct answer label, by inference processing using a first classifier for classifying medical data;

evaluating, as first evaluation, a degree of deviance based on the class likelihood acquired by the likelihood acquisition and a class answer corresponding to the correct answer label;

determining whether the degree of deviance by the first evaluation satisfies a predetermined criterion; and acquiring, from the first medical data, second medical data which is determined to satisfy the predetermined criterion, and evaluating, as second evaluation, based on a similarity of third medical data to be subjected to classification with the second medical data, wherein evaluating as the second evaluation comprises evaluating the similarity using machine learning and based on teacher data given a label corresponding to information indicating whether the data of the first medical data is the data of the second medical data, and wherein the first, second, and third medical data are accessed from a database organized in a storage.

\* \* \* \* \*